United States Patent [19]

Parker et al.

[11] 4,195,632
[45] Apr. 1, 1980

[54] FLUID FLOW VALVE

[75] Inventors: Wendell R. Parker, Moraga; Mark H. Silverman, Redwood City; Willis L. Warner, San Rafael, all of Calif.

[73] Assignee: Cutter Laboratories, Inc., Berkeley, Calif.

[21] Appl. No.: 902,328

[22] Filed: May 3, 1978

[51] Int. Cl.² ................................................ A61J 1/00
[52] U.S. Cl. .............................. 128/272; 128/214 D; 137/68 R
[58] Field of Search ............................ 128/273.1–274, 128/279, 214 D, 214.4, 272.1, DIG. 24; 137/318, DIG. 34

[56] References Cited

U.S. PATENT DOCUMENTS

| 3,110,308 | 11/1963 | Bellamy | 128/214.2 |
| 3,685,795 | 8/1972 | Caster | 251/342 |
| 3,796,218 | 3/1974 | Burke et al. | 128/272 |

FOREIGN PATENT DOCUMENTS 2356397  1/1975  Fed. Rep. of Germany ........ 128/272.3

*Primary Examiner*—Robert W. Michell
*Assistant Examiner*—Milford Juten
*Attorney, Agent, or Firm*—James A. Giblin; Robert E. Allen; Bertram Bradley

[57] ABSTRACT

An improvement in a fluid flow valve is disclosed. The valve comprises a combination of flexible tubing joined to a tubular member having a membrane closing off the passageway in the tubular member. A pointed spike having at least three radially projecting ribs extending longitudinally is located within the tubing adjacent the membrane and is movable by external manipulation of the tubing whereby the spike ruptures the membrane and creates a passageway permitting fluid to flow freely through the tubular member and adjoining tubing.

10 Claims, 7 Drawing Figures

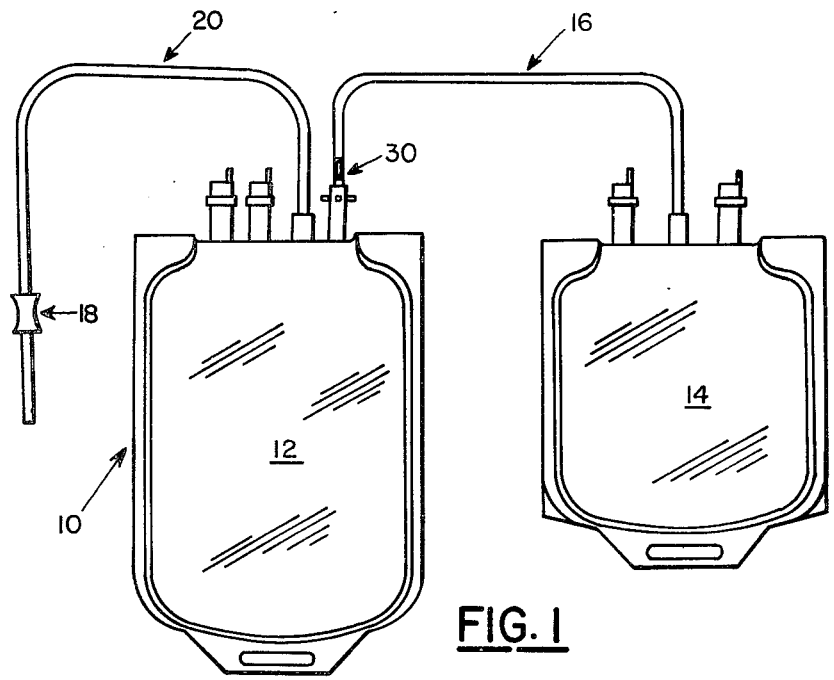
FIG. 1
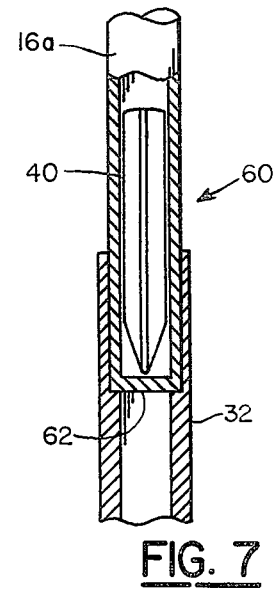
FIG. 7
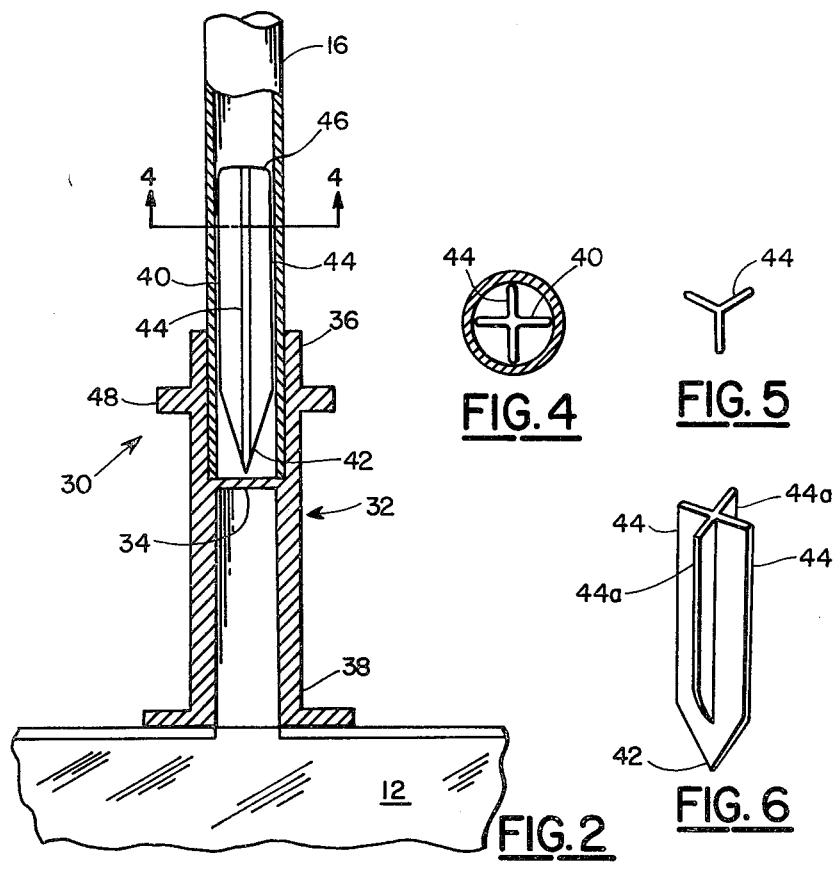
FIG. 2
FIG. 4
FIG. 5
FIG. 6
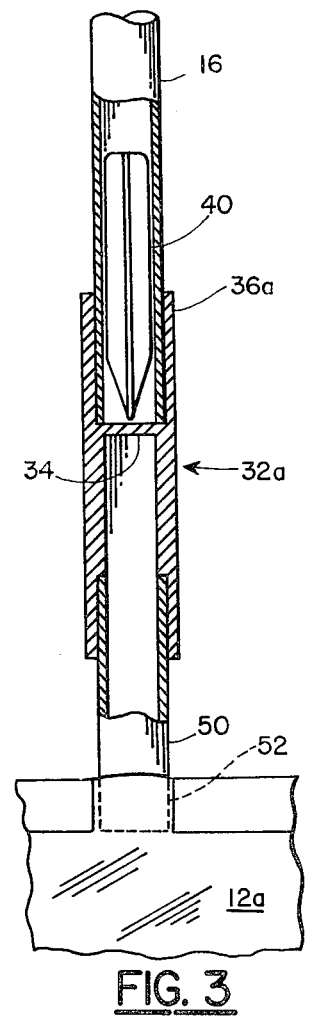
FIG. 3

FLUID FLOW VALVE

BACKGROUND OF THE INVENTION

This invention relates to a fluid flow valve and in particular to one which is intended for use with flexible blood bags and the like but which also can be used as a means for initiating flow of fluid in any conduit system closed by a membrane.

Blood bag systems employing two or more flexible bags interconnected by lengths of flexible tubing are currently in use for separating whole blood into plasma, red cells, platelets and the like in a sterile manner. Frequently, it is necessary to prevent the contents of one bag from flowing through interconnecting tubing into another bag during manipulative steps such as when blood is drawn from a donor into a bag and then centrifuged to separate red cells from the plasma. Externally located valves or clamps may become dislodged or may damage the tubing.

Several internally located valve devices have been developed which are all characterized by having a transverse membrane in the tubing which can be ruptured by a hollow cannula situated within the tubing. The membrane assures there will be no fluid flow from one bag to another until such time the cannula is manipulated to rupture the membrane. For example, U.S. Pat. No. 3,685,795 shows a pointed cannula fixed at one end to the tubing and encased in a sleeve which is secured to a section of tubing containing a membrane. Such a valve device is quite complex in structure and expensive to manufacture. A much simpler valve is disclosed in U.S. Pat. No. 3,110,308. It consists of a pointed hollow unattached cannula in the tubing and a membrane located adjacent the pointed end of the cannula.

By compressing the tubing adjacent the cannula, the cannula can be moved so as to penetrate the membrane and initiate flow of fluid through the tubing. Some cannulas are difficult to move because of excessive drag generated between walls of the tubing and the cannula. Smaller cannulas can be moved more readily but they limit the flow of fluid and they also run the risk of rupturing the bag wall if they are moved too far.

SUMMARY OF THE INVENTION

We have devised a fluid flow valve which is not only inexpensive to manufacture and easily manipulated but also in some preferred embodiments avoids the possibility of rupturing of a container wall. The fluid flow valve of the present invention comprises flexible tubing in a fluid transfer system having at least one container in communication with the tubing, a pierceable membrane in the flow path of the tubing, and a unique spike member lying within the tubing adjacent the membrane. The spike member comprises a longitudinal body having at least three radially projecting ribs which extend longitudinally along the body and converge towards a pointed end. The spike has a particular advantage over tubular cannulas in that, when the spike is moved, only the outside edges of the ribs come into contact with the interior wall surfaces of the tubing and any frictional drag effect is much less than that for a tubular cannula of the same diameter thus allowing for easier manipulation of the spike. Consequently, spikes having diameters significantly greater than tubular cannulas but having no greater drag can be used whereby greater fluid flow can be effected following rupture of the membrane by the spike. Another advantage the spike member has over a tubular cannula is that the pointed end is substantially centrally located and this facilitates rupturing of the membrane.

A preferred form of the fluid flow valve of this invention, particularly when used in a fluid transfer system employing plastic bags, further includes a tubular member interposed between the bag and the flexible tubing. The pierceable membrane lies adjacent the juncture between the tubular member and the tubing. The tubular member has a rigidity such that when the spike member is manipulated through the tubing to puncture the membrane and becomes positioned within the tubular member, the tubular member cannot be manipulated so as to move the spike member beyond the tubular member. Rupturing of the bag by the spike is thus prevented.

The invention can be better understood and the advantages will become apparent from the following description of some preferred embodiments and as illustrated in the drawings.

BRIEF DESCRIPTION OF THE DRAWINGS

FIG. 1 illustrates a multi-bag blood processing system containing a fluid flow valve of the present invention.

FIG. 2 is a side view in cross-section of a preferred embodiment of the fluid flow valve of this invention.

FIG. 3 is a side view in cross-section of another embodiment of the fluid flow valve of this invention.

FIG. 4 is a sectional view taken along line 4—4 of FIG. 2.

FIG. 5 is an end view of another form of the spike member of the fluid flow valve.

FIG. 6 is representative of an alternate form of a spike member.

FIG. 7 is a sectional view of a portion of still another form of the fluid flow valve.

DETAILED DESCRIPTION OF PREFERRED EMBODIMENTS

Referring to the drawings, FIG. 1 illustrates a multiple bag system 10 which comprises a blood collection bag 12 and a blood component receiving bag 14 connected by flexible tubing 16. Bag 12 is typically joined to a donor needle assembly 18 by tubing 20. Each bag 12 or 14 may have one or more ports 22 for access to the contents after collection and processing.

The fluid flow valve 30 of this invention, which controls the flow of fluid between bags 12 and 14, is best illustrated in FIGS. 2 and 4. Valve 30 comprises a tubular member 32 with a pierceable transverse membrane 34 intermediate the ends 36 and 38. Flexible tubing 16 is sealingly connected to end 36 and end 38 is sealed to and in communication with bag 12. A spike member 40 is positioned within tubing 16 and has a pointed end 42 facing membrane 34 of tubular member 32.

The spike member 40 as shown in FIGS. 2-4 comprises four ribs 44 radiating from a common axis and tapering to the pointed end 42. The spike member can have three ribs generally equally spaced as shown in FIG. 3 or it can have five or more ribs. A spike with four ribs is preferred. The spike member can be made of any material which allows it to be manipulated externally through the tubing 16 to rupture membrane 34. Preferably the length of the spike member is substantially no greater than the length of tubular member 32 so that its pointed end 42 does not extend into the bag 12 when the end 46 is in line with end 36 of the tubular member, thus avoiding possible rupture of the bag wall. The spike member can have other features such as that shown in FIG. 6. Here two opposing ribs 44 converge at the pointed end 42 and the other two opposing ribs 44a taper to the axis at a spot rearwardly of the pointed end.

The spike member is made preferably as wide as possible without creating so tight a fit within tubing 16 that it cannot be readily manipulated for movement through membrane 34. In some instances, the spike can be coated with an inert lubricant such as silicone oil to facilitate its movement within the tubing. Following external manipulation of tubing 16 to force the spike through membrane 34, edges of the ruptured membrane exert pressure against the ribs of the spike and help to prevent its progression into the bag.

Tubular member 32 preferably is made of the same material as that of the tubing 16 and bag 12 so that heat or solvent bonding to the bag and tubing can be more readily effected. The walls of the tubular member 32 are generally somewhat thicker than the wall of tubing 16 which imparts sufficient rigidity to the member such that spike 40, once it has been forced within the confines of tubular member 32, cannot be externally manipulated further and thus prevents the spike or any significant part of the pointed end from entering bag 12. The tubular member 32 as shown in FIG. 2 has an annular ledge 48 near end 36 which aids the user in getting a firmer grasp of the member while the spike is being manipulated through tubing 16. The presence of ledge 48 is not critical, however, to the function provided by the tubular member.

Another embodiment of the fluid flow valve of this invention is illustrated in FIG. 3. Here the tubular member 32a communicates with bag 12a by being sealed to a relatively short piece of tubing 50 whose inner end 52 is sealed between two sealed sheets comprising bag 12a.

Although tubing 16 is shown in FIGS. 2 and 3 as being sealed within tubular members 32 or 32a, alternatively tubing 16 can be made to fit over and enclose the ends 36 or 36a of the tubular members.

A further embodiment 60 of the fluid flow valve is shown in FIG. 7. Here the pierceable membrane 62 is integrally a part of tubing 16a.

As an example of how the fluid flow valve of this invention may be used, following venipuncture with the needle of needle assembly 18, blood is drawn from a donor into bag 12, tubing 20 is sealed off near the bag and the entire system 10 is centrifuged allowing separation of the plasma from the red blood cells. Spike 40 is externally manipulated as for example, by compressing tubing 16 adjacent the blunt end 46 which forces spike 40 through membrane 34, causing the ruptured membrane to spread, thus creating a passageway between each of two adjacent ribs 44. The plasma is then expressed from bag 12 through tubing 16 into bag 14 where it may be stored for further processing.

Although several examples of the fluid flow valve of the present invention have been disclosed, these should be construed as illustrative only and the scope of the invention is intended to be limited only by the following claims.

We claim:

1. In a system for handling fluids which includes at least one container in communication with flexible tubing, a fluid flow valve system which comprises:
   a pierceable membrane lying transversely in the flow path of the tubing and adapted to prevent fluid flow therethrough;
   a spike member having a pointed end and positioned within a portion of the tubing adjacent the membrane, the spike member being unattached and capable of movement within the tubing and comprising a longitudinal body having at least three radially projecting ribs extending longitudinally substantially the full length of the body and converging towards the pointed end;
   the spike member being adapted for rupturing the membrane by external manipulation of the tubing so as to create a passageway for flow of fluid in the space between any two adjacent ribs and the ruptured membrane.

2. The valve system of claim 1 wherein the spike member has four ribs spaced generally equidistant from each other.

3. In a fluid transfer system which comprises flexible tubing communicating with the interior of at least one container, a fluid flow valve system which comprises:
   a tubular member having one end in communication with the interior of said one container and its other end joined to the tubing;
   a pierceable membrane lying transversely in the tubular member and adapted to prevent fluid flow therethrough;
   a spike member having a pointed end and located within a portion of the tubing adjacent the membrane, the spike member being unattached and capable of movement within the tubing and comprising a longitudinal body having at least three radially projecting ribs extending longitudinally substantially the full length of the body and converging towards the pointed end;
   the tubular member having a rigidity sufficient to prevent the spike member from being further manipulated after it has been externally manipulated through the tubing to rupture the membrane and moved to a position within the tubular member;
   the spike member creating a passageway for flow of fluid in the space between any two adjacent ribs and the ruptured membrane.

4. The valve of claim 3 wherein the spike has four ribs spaced substantially equally from each other.

5. The valve of claim 4 wherein one pair of opposing ribs converge to meet at the pointed end and the other pair of opposing ribs converge at a spot on the axis of the spike rearward of the pointed end.

6. The valve of claim 3 wherein the membrane is located intermediate the two ends of the tubular member.

7. The valve of claim 3 wherein the membrane is integral with the tubular member.

8. The valve of claim 3 wherein the membrane is integral with the tubing.

9. The valve of claim 3 wherein said one end of the tubular member is secured directly to a wall portion of said one container.

10. The valve of claim 3 wherein said one end of the tubular member is spaced from said one container by a length of interconnecting tubing.

* * * * *